(12) United States Patent
Zinobile et al.

(10) Patent No.: US 8,563,773 B2
(45) Date of Patent: Oct. 22, 2013

(54) EDUCTOR-BASED REACTOR AND PUMP AROUND LOOPS FOR PRODUCTION OF ACETIC ACID

(75) Inventors: Raymond Zinobile, Houston, TX (US); Michael Lakin, Katy, TX (US); Ashok Rakhe, Corpus Christi, TX (US); Ronald Shaver, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 372 days.

(21) Appl. No.: 12/970,315

(22) Filed: Dec. 16, 2010

(65) Prior Publication Data

US 2012/0157710 A1 Jun. 21, 2012

(51) Int. Cl.
*C07C 51/12* (2006.01)
*C07C 51/10* (2006.01)

(52) U.S. Cl.
USPC ........................................... 562/519; 562/517

(58) Field of Classification Search
CPC .................................................... C07C 51/235
See application file for complete search history.

(56) References Cited

U.S. PATENT DOCUMENTS

| | | | | |
|---|---|---|---|---|
| 3,522,017 | A | * | 7/1970 | Barfield, Jr. ................. 422/201 |
| 3,769,329 | A | | 10/1973 | Paulik et al. |
| 4,140,625 | A | * | 2/1979 | Jensen ......................... 208/146 |
| 5,001,259 | A | | 3/1991 | Smith et al. |
| 5,026,908 | A | | 6/1991 | Smith et al. |
| 5,144,068 | A | | 9/1992 | Smith et al. |
| 5,364,963 | A | | 11/1994 | Minami et al. |
| 5,672,744 | A | | 9/1997 | Kagotani et al. |
| 6,114,576 | A | | 9/2000 | Leet et al. |
| 6,175,039 | B1 | | 1/2001 | Voss |
| 7,465,823 | B2 | | 12/2008 | Bhaskaran et al. |
| 2006/0281944 | A1 | | 12/2006 | Hosono et al. |

FOREIGN PATENT DOCUMENTS

WO WO 2012/039973 A1 3/2012

OTHER PUBLICATIONS

J. H. Jones, "The Cativa Process for the Manufacture of Acetic Acid", Platinum Metals Review, 44 (3); pp. 94-105 (2002).
Written Opinion for PCT/US2011/063713 mailed Jan. 3, 2013.
Pakistan Examination Report for PK Application No. 902/2011 dated Jan. 16, 2013.
International Search Report and Written Opinion mailed Aug. 3, 2012 in corresponding International Application No. PCT/US2011/063713.
International Preliminary Report on Patentability mailed Mar. 21, 2013 in corresponding International Application No. PCT/US2011/063713.

* cited by examiner

*Primary Examiner* — Paul A Zucker (57) ABSTRACT

Eductor mixers are used to mix the reaction medium in a carbonylation reactor. A portion of the reaction solution withdrawn from the reactor and directed through a pump around loop. The pump around loop is fed back to the reactor through the eductor mixers. In addition, a pump around loop may pass through one or more steam generators and/or heat exchangers.

22 Claims, 5 Drawing Sheets

EDUCTOR-BASED REACTOR AND PUMP AROUND LOOPS FOR PRODUCTION OF ACETIC ACID

FIELD OF THE INVENTION

The present invention relates to an improved method for the manufacture of acetic acid and, in particular, to improvements to the acetic acid production system including the implementation of an eductor-based reactor and one or more pump around loops.

BACKGROUND OF THE INVENTION

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises methyl acetate, water, acetic acid, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in J. H. Jones, "The Cativa™ Process for the Manufacture of Acetic Acid," Platinum Metals Review, 44 (3): 94-105 (2002), the entire contents and disclosure of which is hereby incorporated by reference.

The carbonylation reactor typically involves an impeller driven mixing system. Impeller driven mixing systems generally incorporate at least one impeller mounted on a rotating shaft. Such systems may be said to have an axial longitudinal flow parallel to the axis of the rotating shaft and/or a radial flow parallel to the radially extending blades mounted on the shaft. The impeller may thus be a radial flow impeller, which projects fluid in a radial direction towards a wall of a tank or chamber in which the impeller is housed, or alternatively, the impeller may be an axial flow impeller, which comprises radially extending blades that are pitched at an angle so as to direct the fluid flow in an axial direction. These and other mechanical agitation mixing methods requiring a rotating shaft are energy intensive, require high capital installations, which includes the shaft to reactor seal system. These reactors utilize mechanical seals, which have finite life cycles and rigorous maintenance requirements.

The reaction solution from the carbonylation reactor contains unreacted starting materials as well as components of the reaction medium, including catalyst. U.S. Pat. No. 5,672,744 discloses a process for the preparation of acetic acid, which comprises carbonylating methanol with carbon monoxide in a carbonylation reactor, in the presence of a reaction fluid comprising a rhodium catalyst, methyl iodide, an iodide salt, methyl acetate and water, while continuously withdrawing the reaction fluid from the reactor and introducing it into a flash zone to separate it into an evaporated part and an unevaporated part.

The carbonylation reaction is exothermic and the heat of the reaction must be regulated to control reaction temperatures. The heat of the reaction typically is transferred to the flasher along with the reaction solution. The flasher operates at a lower pressure than the reactor, which results in a temperature decrease of the reaction solution.

The heat of the reaction may also be recovered. U.S. Pat. No. 6,175,039 discloses removing the heat of reaction from the highly exothermic process by using a steam boiler heated by the pump-around stream. The heat from the reaction may also be transferred to other systems. U.S. Pat. No. 6,114,576 discloses a process for the production of carboxylic acid in the presence of solid catalyst particles that uses the exothermic heat of reaction with high efficiency in recovering the carboxylic acid product. This process uses indirect heat exchange to transfer the heat of reaction to another stream, without the need for an additional heat transfer fluid such as steam. U.S. Pat. No. 7,465,823 discloses a process and system in which a portion of the heat produced during the production of the acetic acid is transferred to the vinyl acetate production and/or purification process and system to facilitate production and/or purification of the vinyl acetate product.

As will be appreciated by one of skill in the art, there is incentive and a need for improvement to existing processes for the production of acetic acid. The present invention provides some such improvements.

SUMMARY OF THE INVENTION

Embodiments of the present invention are to improved methods for the preparation of acetic acid. In one embodiment, a process for producing acetic acid is provided, comprising the steps of: reacting carbon monoxide with at least one reactant in a eductor-based reactor containing a reaction medium to produce a reaction solution comprising acetic acid, wherein the at least one reactant is selected from the group consisting of methanol, methyl acetate, methyl formate, dimethyl ether and mixtures thereof, and wherein the reaction medium comprises water, acetic acid, methyl acetate, methyl iodide, and a catalyst, wherein the eductor-based reactor comprises one or more eductor mixers; withdrawing the reaction solution from the eductor-based reactor; separating a portion of the reaction solution to form a pump around stream; and feeding a portion of the pump around stream to at least one of the one or more eductor mixers to provide mixing of the reaction medium in the eductor-based reactor.

In some embodiments of the present invention, the process further comprises: feeding a remaining portion of the reaction solution forward to a flasher to produce a crude product and a catalyst recycle stream, wherein the pump around stream is separated prior to the introduction to the flasher. In preferred embodiments, the flow rate of the pump around stream is at least 1.2 times greater than the flow rate of the remaining portion of the reaction solution forwarded to the flasher. In other embodiments, the process further comprises: passing a portion of the pump around stream through one or more steam generators to produce an exiting process stream and steam. In still other embodiments, the process further comprises: feeding a portion of the exiting process stream to at least one of the one or more eductor mixers to provide mixing of the reaction medium in the eductor-based reactor. In certain embodiments, the exiting process stream has a temperature that is less than the temperature of the reaction solution withdrawn from the eductor-based reactor. In other embodiments of the present invention, the process further comprises the step of: passing a portion of the pump around stream through one or more heat exchangers to produce an outflow and in others, the step of: feeding a portion of the outflow to at least one of the one or more eductor mixers to provide mixing of the reaction medium in the eductor-based reactor. In certain embodiments, 20% to 100% of the reaction solution withdrawn from the eductor-based reactor is separated as the pump around stream. In other embodiments, at least 50% of the reaction solution withdrawn from the eductor-based reactor is separated as the pump around stream. In some embodiments of the present invention, the one or more eductor mixers each have a discharge to motive ratio of at least 2:1.

In another embodiment, the invention is to a process for producing acetic acid, comprising the steps of: reacting carbon monoxide with at least one reactant in a reactor containing a reaction medium to produce a reaction solution comprising acetic acid, wherein the at least one reactant is selected from the group consisting of methanol, methyl acetate, methyl formate, dimethyl ether and mixtures thereof, and wherein the reaction medium comprises water, acetic acid, methyl acetate, methyl iodide, and a catalyst; withdrawing the reaction solution at a first flow rate from the reactor; separating a portion of the reaction solution to form a pump around stream; separating a remaining portion of the reaction solution that is forwarded to a flasher, wherein the flow rate of the pump around stream is at least 1.2 times greater than the flow rate of the remaining portion of the reaction solution forwarded to flasher; passing a portion of the pump around stream through one or more steam generators to produce an exiting process stream and steam; and feeding a portion of the exiting process stream to the reactor. In accordance with various embodiments of the present invention, the process may further comprise one or more of the following steps: feeding a portion of the exiting process stream to at least one of the one or more eductor mixers to provide mixing of the reaction medium in the eductor-based reactor; passing a portion of the exiting process stream through one or more heat exchangers to produce an outflow; and introducing the remaining portion of the reaction solution to the flasher to produce a crude product and a catalyst recycle stream, wherein the pump around stream is separated prior to the introduction to the flasher.

Further embodiments of the invention are directed to a process for producing acetic acid, comprising the steps of: reacting carbon monoxide with at least one reactant in a reactor containing a reaction medium to produce a reaction solution comprising acetic acid, wherein the at least one reactant is selected from the group consisting of methanol, methyl acetate, methyl formate, dimethyl ether and mixtures thereof, and wherein the reaction medium comprises water, acetic acid, methyl acetate, methyl iodide, and a catalyst; withdrawing the reaction solution at a first flow rate from the reactor; separating a portion of the reaction solution to form a pump around stream; separating a remaining portion of the reaction solution that is forwarded to a flasher, wherein the flow rate of the pump around stream is at least 1.2 times greater than the flow rate of the remaining portion of the reaction solution forwarded to flasher; passing a portion of the pump around stream through one or more heat exchangers to produce an outflow; and feeding a portion of the outflow to the reactor. In accordance with various embodiments of the present invention, the process may further comprise one or more of the following steps: feeding a portion of the outflow to at least one of the one or more eductor mixers to provide mixing of the reaction medium in the eductor-based reactor; passing a portion of the pump around stream through one or more steam generators to produce an exiting process stream and steam; and introducing the remaining portion of the reaction solution to the flasher to produce a crude product and a catalyst recycle stream, wherein the pump around stream is separated prior to the introduction to the flasher.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

The present invention relates to improved processes for the manufacture of acetic acid. In particular, the present invention uses an eductor-based reactor in an acetic acid production system. The feed components, carbon monoxide and methanol or its derivatives, along with recycle streams are introduced in the lower portion of the reactor to form a reaction medium. Eductor-based reactors of the present invention uses one or more eductor mixers to mix the reaction medium. The eductor mixers may promote circulation throughout the reactor. The reactor produces a reaction solution that may be purified to recover the acetic acid. Prior to purification, a portion of the reaction solution may be separated as a pump around stream and returned to the reactor via one or more pump around loops. In one embodiment, the pump around streams may be withdrawn directly from the reactor. Preferably, one of the pump around streams may be directed to eductor mixers and the discharge thereof mixes the reaction medium. In another embodiment, the heat of the carbonylation reaction may be recovered in the pump around loops. In addition, the pump around loops may provide temperature control for the carbonylation reaction.

The carbonylation reactor of the present invention is an "eductor-based" reactor that includes one or more eductor mixers. The mixers used in the eductor-based reactor are preferably one or more types of jet mixers (pumps) that make use of the momentum of one fluid (primary) to move another fluid (secondary). The eductor-based reactor may also include ejectors, exhausters, injectors, siphons or other types of venturi mixers. Conversely to an mechanical agitator-based reactor or a stirred vessel (e.g., continuous stirred-tank reactor (CSTR), the eductor-based reactor of the present invention preferably contains no moving parts within the reactor for mixing the reaction medium, thereby improving on-stream operational reliability. Instead, the mixing of the reaction medium is conducted by the discharge of one or more eductor mixers. Use of the eductor-based reactor also eliminates the need for a seal mounted on the reactor. In preferred embodiments of the present invention, the supply to the eductor mixers or primary motive fluid is taken from a portion of the reaction solution that is withdrawn from the reactor, e.g., via one or more pump around streams.

Figure 1A:
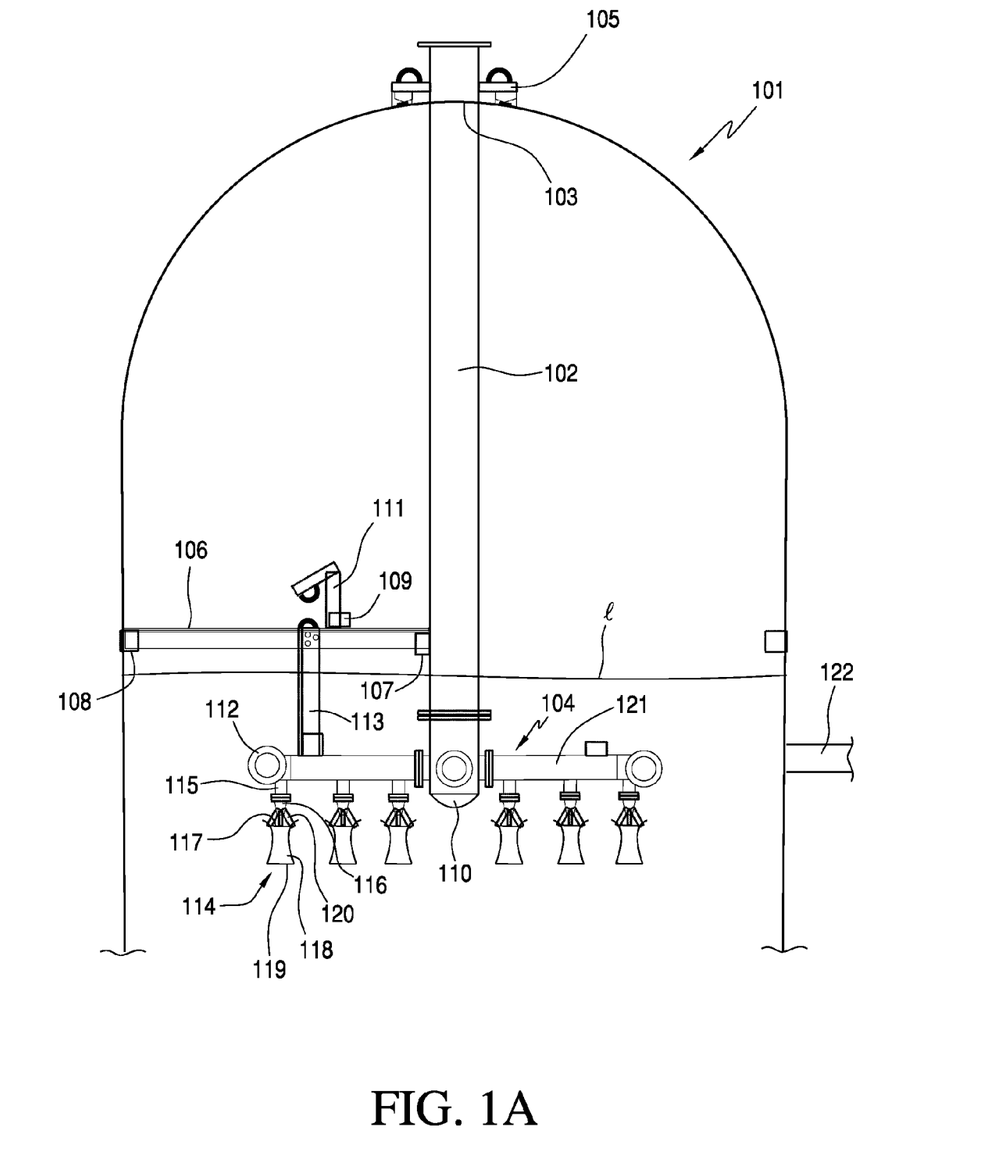
FIG. 1A is a partial cut-away view of an eductor-based reactor in accordance with one embodiment of the present invention.

FIG. 1A is a partial cutaway view of an eductor-based reactor 101 of one embodiment of the present invention. The internal surface of the shell of the eductor-based reactor 101 may comprise any suitable material, for example glass, ceramic, specialty thermoplastic, thermoset plastic, high chemical and heat resistant elastomer, nickel-molybdenum alloy such as HASTELLOY™ B-3™ alloy (Haynes International), or zirconium alloy such as Zirc™ 702 alloy (United Titanium Inc.). As shown in FIG. 1A, supply pipe 102 extends through opening 103 in the top of reactor 101 and is connected at a distal end to manifold 104. Supply pipe 102 may be mounted to reactor 101 by pad 105 that is fixed to an outer portion of reactor 101. In some embodiments, supply pipe 102 may be removably mounted. In addition, one or more gaskets, such as a sealing rings, may be provided to provide a sealing connection. Advantageously, because supply pipe 102 preferably remains stationary in opening 103, there is less wear on the gaskets than in designs utilizing a mechanical stirrer. As shown in FIG. 1A, support beam 106 may be connected to supply pipe 102 at bracket 107. Bracket 108 along a sidewall within reactor 101 assists to stabilize supply pipe 102 in a vertically mounted position. Lifting arm 111 is affixed to support beam 106 via bracket 109. As additionally shown in FIG. 1A, support beam 106 in conjunction with stabilizer beam 113 may stabilize manifold 104. In certain embodiments of the present invention, a plurality of support beams are used to stabilize the various components of eductor-based reactor 101.

Figure 1B:
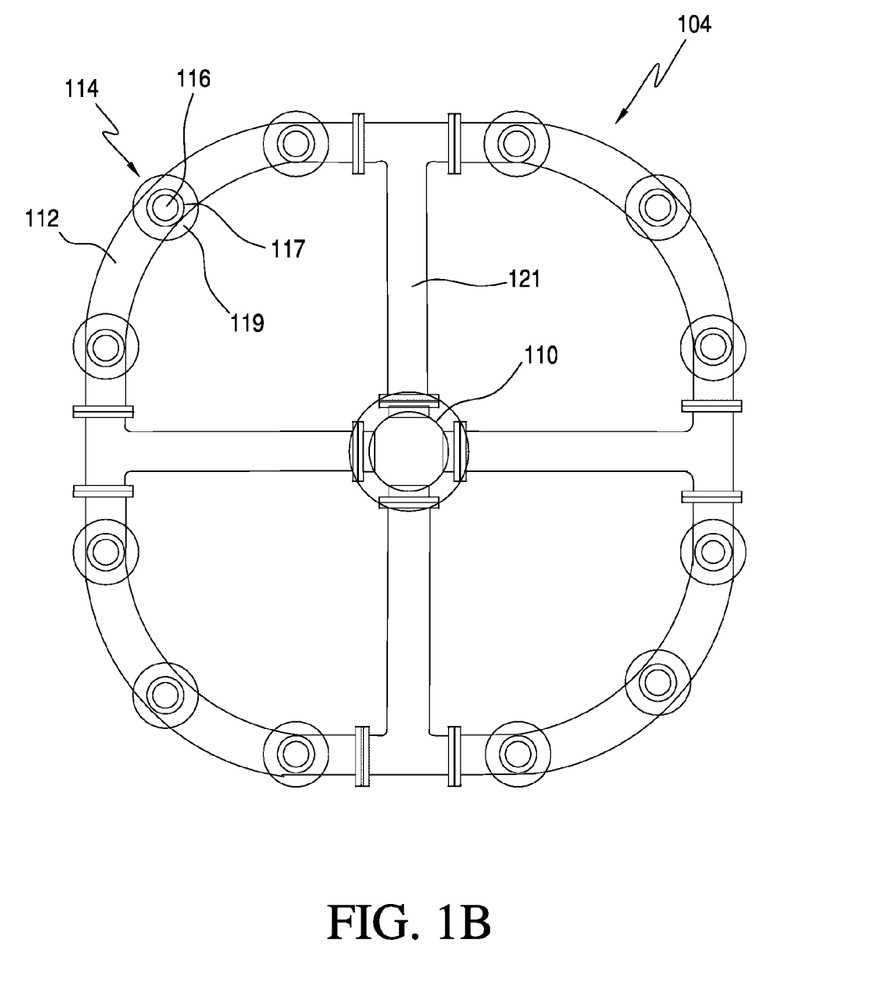
FIG. 1B is a bottom view of a manifold for an eductor-based reactor in accordance with one embodiment of the present invention.

Manifold 104 is preferably positioned below the liquid level l in eductor-based reactor 101. As shown in FIGS. 1A and 1B, manifold 104 comprises a distributor hub 110, distributor conduits 121, and eductor conduits 112. In some embodiments, distributor hub 110 may be directly connected to supply pipe 102, one or more distribution conduits 121 may be connected to distributor hub 110, and one or more eductor conduits 112 may be connected to the distribution conduits 121. In certain embodiments, stabilizer beam 113 may be connected to the distribution conduits 121 and support beam 106. As shown in FIG. 1B, manifold 104 may be in a ring or circle arrangement. However, there is no limit on the number of conduits, and other manifold arrangements may be used within the scope of the present invention. In certain embodiments, the components of manifold 104, when disassembled, may be individually sized as to fit through opening 103 and/or a standard size (i.e., 20 inch to 24 inch diameter) manway, which may allow easy removal of the components for maintenance.

Manifold 104, as shown in FIGS. 1A and 1B, further comprises one or more eductor mixers 114. Eductor mixers 114 are preferably mounted to eductor conduits 112, but may also be mounted directly to distribution hub 110 or distribution conducts 121. In preferred embodiments, eductor mixers 114 extend into the reaction medium and are positioned below the liquid level 1. In some embodiments, the one or more eductor mixers 114 include stem 115, nozzle 116, openings 117, diffuser 118, and discharge orifice 119. Nozzle 116 may be connected to diffuser 118 by one or more ribs 120 with openings 117 therebetween. In certain embodiments, secondary fluid for each eductor mixer 114 may be taken from the reaction medium through openings 117. The primary fluid supply for the eductor mixers 114 may be withdrawn from the reaction solution that exits out of pipe 122 as a pump around stream, as discussed herein. Preferably, eductor mixers 114 of the present invention have a motive to discharge ratio of at least 1:2, e.g., at least 1:3 or at least 1:5, so as to provide sufficient mixing of the reaction medium.

In some embodiments, each eductor mixer 114 of manifold 104 may extend vertically downward (zero degrees) to effectuate mixing. In other embodiments, the eductor mixers 114 are angled at any suitable angle such as less than 90 degrees (horizontally sideways), e.g., less than 60 degrees or less than 45 degrees. In addition, in certain embodiments, the eductor mixers 114 of manifold 104 may include both eductor mixers 114 positioned vertically downward and eductor mixers 114 positioned at an angle. In some embodiments, the angles of the eductor mixers 114 may alternate between vertically downward and angled. In one exemplary embodiment, every other eductor mixer 114 is positioned at an angle of zero degrees to provide straight-down or direct axial flow, while the in-between eductor mixers 114 are positioned at an angle of 45 degrees. The angles and positioning of the eductor mixers 114 may account for the varying reactor size and design including length, width, fluid entrance and exit locations, main fluid nozzle location, internal baffles or other anti-vortex device location.

Any suitable eductor mixer 114 may be used in embodiments of the present invention. Eductor mixers 114 may be constructed of any suitable material, including but not limited to metals or metal alloys such as, for example, HASTELLOY™ B-3™ alloy (Haynes International), zirconium alloy such as Zirc™ 702 alloy (United Titanium Inc.), ceramic, composite ceramic material/engineered reinforced ceramic such as, for example, metal reinforced ceramic, a polymer such as, for example, a specialty thermoplastic or polymer composite material. The number of eductor mixers may be determined based on the size and configuration of the reactor. In one embodiment, the number of eductor mixers 114 connected to the manifold 104 may range from 1 to 20, e.g., 4 to 16 or from 6 to 12. Although additional eductor mixers may be used, the efficiency may not show significant improvements above 20 eductor mixers. Each eductor mixer 114 may have a length from 10 to 110 cm, e.g., 30 to 100 cm or 50 to 90 cm.

In accordance with some embodiments of the present invention, one or more pump around loops may be used to return a portion of the reaction solution to the reactor. At least one of the pump around loops is preferably directed to supply pipe 102, and primary fluid is distributed with manifold 104 and/or eductor mixers 114. In addition, the pump around loops may be used to recover the heat from the carbonylation reactor and/or regulate the temperature of the reactor.

The present invention may be applied in any methanol carbonylation process. Exemplary carbonylation systems that may be used with embodiments of the present invention include those described in U.S. Pat. Nos. 7,223,886, 7,005,541, 6,657,078, 6,339,171, 5,731,252, 5,144,068, 5,026,908, 5,001,259, and 4,994,608, and U.S. Pub. Nos. 2008/0287706, 2008/0293966, 2009/0107833, and 2009/0270651, the entire contents and disclosures of which are hereby incorporated by reference. A carbonylation system may comprise a carbonylation section and a purification section. Any suitable purification section may be used in combination with any of the embodiments of the present invention. Suitable purification sections are described in the patents referenced above and typically include a light ends column, a drying column, one or more columns for removal of permanganate reducing compounds (PRC's), guard beds, vent scrubbers, and/or heavy ends columns.

Figure 2:
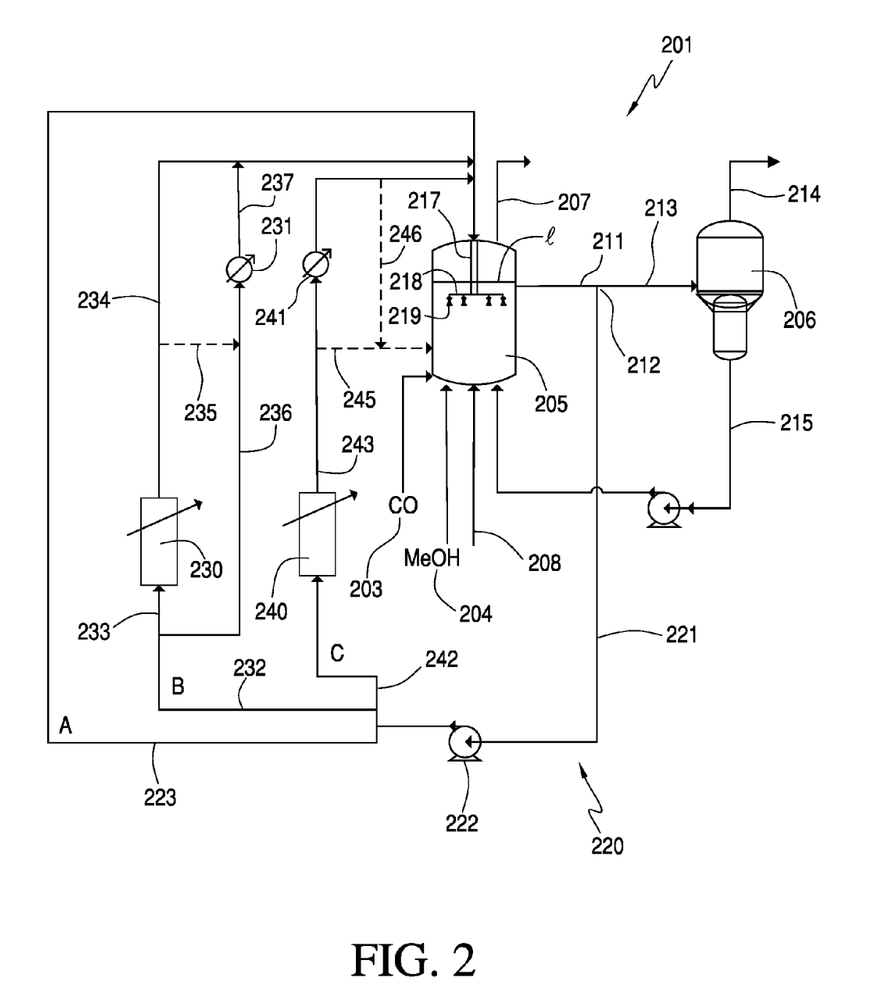
FIG. 2 is an exemplary schematic diagram for acetic acid production having an eductor-based reactor and pump around loops in accordance with one embodiment of the present invention.

An exemplary carbonylation section 201 is shown in FIG. 2. Carbonylation section 201 comprises carbon monoxide feed stream 203, reactant feed stream 204, eductor-based reactor 205, and flasher 206. Carbon monoxide and at least one reactant are fed by feed streams 203 and 204, respectively, to a lower portion of eductor-based reactor 205. Reactant feed stream 204 supplies at least one reactant selected from the group consisting of methanol, methyl acetate, methyl formate, dimethyl ether and/or mixtures thereof, to eductor-based reactor 205. In preferred embodiments, reactant feed stream 204 supplies methanol and methyl acetate. Optionally, reactant feed stream 204 may be connected to one or more vessels (not shown) that store fresh reactants for the carbonylation process. In addition, there may be a methyl iodide storage vessel (not shown) and/or catalyst vessel (not shown) connected to eductor-based reactor 205 for supplying fresh methyl iodide and catalyst as needed to maintain reaction conditions. In other embodiments, all or some of the methanol and/or reactive derivatives thereof supplied to eductor-based reactor 205 may be in the form of scrubbed methanol from another location in the system or as a product or by-product of another system.

One or more recycle feed streams from carbonylation section 201 may be fed to reactor 205 via line 208. As discussed herein, recycle feed stream 208 may comprise the components of the reaction medium, as well as residual and/or entrained catalyst and acetic acid. Although one recycle feed stream 208 is shown in FIG. 2, there may be multiple streams that are fed separately to eductor-based reactor 205. For example, one or more recycle feed streams from a purification section may be fed to reactor 205 via line 208. In preferred embodiments, the recycle feed streams fed via line 208 are introduced in the lower portion of reactor 205. Because the recycle feed streams contain components used in the carbonylation reaction, it is preferred to introduce the recycle feed in the lower portion of the reactor along with the fresh carbon monoxide and reactants. In an optional embodiment, a portion of the recycle feed stream may be introduced as the supply for the eductor mixers.

In certain embodiments of the invention, reactant feed stream 204 comprises methanol and/or reactive derivatives thereof. Suitable reactive derivatives of methanol include methyl acetate, dimethyl ether, methyl formate and mixtures thereof. In one embodiment, a mixture of methanol and reactive derivatives of methanol is used as a reactant in the process of the present invention. Preferably, methanol and/or methyl acetate are used as reactants. At least some of the methanol and/or reactive derivatives thereof will be converted to, and hence be present as, methyl acetate in the reaction medium by reaction with acetic acid product or solvent. The concentration of methyl acetate in the reaction medium is preferably in the range from 0.5 wt. % to 70 wt. %, e.g., from 0.5 wt % to 50 wt. %, or from 1 wt. % to 35 wt. %, of the total weight of the reaction medium.

Carbon monoxide feed stream 203 may be essentially pure or may contain small amounts of inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low (e.g., less than 1 bar partial pressure or less than 0.5 bar partial pressure), as its presence may result in the formation of hydrogenation products. The partial pressure of carbon monoxide in the reaction is preferably in the range from 1 bar to 70 bar, e.g., from 1 bar to 35 bar, or from 1 bar to 15 bar.

In some embodiments of the invention, within eductor-based reactor 205, methanol is reacted with carbon monoxide in a homogeneous catalytic reaction system comprising a reaction solvent, methanol and/or reactive derivatives thereof, a Group VIII catalyst, at least a finite concentration of water and optionally an iodide salt.

Suitable Group VIII catalysts include rhodium and/or iridium catalysts. When a rhodium catalyst is utilized, the rhodium catalyst may be added in any suitable form such that rhodium is in the catalyst solution as an equilibrium mixture including $[Rh(CO)_2I_2]^-$ anion, as is well known in the art. Preferably, the catalyst is a rhodium diiodide dicarbonyl anion that is ionically bound to a suitable resin, e.g., polyvinylpyridine. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259, 5,026,908 and 5,144,068, the entireties of which are hereby incorporated by reference.

When an iridium catalyst is utilized, the iridium catalyst may comprise any iridium-containing compound that is soluble in the reaction medium. The iridium catalyst may be added to the reaction medium for the carbonylation reaction in any suitable form that dissolves in the reaction medium or is convertible to a soluble form. Examples of suitable iridium-containing compounds that may be added to the reaction medium include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)^-_2Br_2]^-H+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$ and hexachloroiridic acid $[H_2IrCl_6]$. Chloride-free complexes of iridium such as acetates, oxalates and acetoacetates are usually employed as starting materials. The iridium catalyst concentration in the reaction medium is generally in the range of 100 to 6000 ppm. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

A halogen co-catalyst/promoter is generally used in combination with the Group VIII metal catalyst component. Methyl iodide is a preferred as the halogen promoter. Preferably, the concentration of halogen promoter in the reaction medium is in the range 1 wt. % to 50 wt. %, and preferably 2 wt. % to 30 wt. %.

The halogen promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention, as described in EP0849248, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the reaction medium and/or any liquid process streams recycled to the eductor-based reactor from the purification and acetic acid recovery stage. When used, the promoter is suitably present in the reaction medium at a molar ratio of promoter to metal catalyst of 0.5:1 to 15:1, preferably 2:1 to 10:1, more preferably 2:1 to 7.5:1. A suitable promoter concentration is 400 to 5000 ppm.

Water may be formed in situ in the reaction medium, for example, by the esterification reaction between methanol reactant and acetic acid product. In some embodiments, water is introduced to the eductor-based reactor 205 together with or separately from other components of the reaction medium. Water may be separated from the other components of reaction composition withdrawn from eductor-based reactor 205 and may be recycled in controlled amounts to maintain the required concentration of water in the reaction medium. Preferably, the concentration of water maintained in the reaction medium is in the range from 0.1 wt. % to 16 wt. %, e.g., from 1 wt. % to 14 wt. %, or from 1 wt. % to 10 wt. % of the total weight of the reaction composition.

In accordance with a preferred carbonylation process of the present invention, the desired reaction rates are obtained even at low water concentrations by maintaining, in the reaction medium, an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In eductor-based reactor 205, the reaction medium is maintained, preferably automatically, at a predetermined level. This predetermined level may remain substantially constant during normal operation. Into eductor-based reactor 205, methanol, carbon monoxide, and sufficient water may be continuously introduced as needed to maintain at least a finite concentration of water in the reaction medium. In some embodiments, carbon monoxide is continuously introduced into eductor-based reactor 205 via line 203. Carbon monoxide feed 203 is introduced at a rate sufficient to maintain the desired total reactor pressure. The temperature of eductor-based reactor 205 may also be controlled using heat exchangers in one or more pump around loops, as illustrated in FIG. 2.

Acetic acid is typically manufactured in a liquid phase reaction at a temperature from about 160° C. to about 220° C. and a total pressure from about 20 bar to about 50 bar. In some embodiments of the invention, eductor-based reactor 205 is operated at a temperature from 150° C. to 250° C., e.g., from 155° C. to 235° C., or from 160° C. to 220° C. Certain embodiments of the present invention are directed to methods for the synthesis of acetic acid where the carbonylation reaction is performed at temperatures elevated to above about 190° C. Exemplary reaction temperatures for elevated-temperature carbonylation are about 190° C. to about 225° C., including about 200° C. to about 220° C. The elevated reaction temperature may facilitate lowering of the reactor catalyst concentration and increasing acetic acid production rates. The pressure of the carbonylation reaction is preferably from 10 to 200 bar, more preferably 10 to 100 bar and most preferably 15 to 50 bar.

In some embodiments of the invention, a gaseous/vapor purge stream is vented via line 207 from the eductor-based reactor 205 to at least prevent buildup of gaseous by-products, inerts and maintain a set carbon monoxide partial pressure at a given total reactor pressure. The gaseous purge stream may be scrubbed with acetic acid and/or methanol in one or more recovery units to recover low boiling point components. In some embodiments, the gaseous purge stream may be condensed and fed to a recovery unit (not shown), which may return low boiling point components to the eductor-based reactor 205. The low boiling point components may comprise methyl acetate and/or methyl iodide. Carbon monoxide in the gaseous purge stream may be purged or fed to the base of flasher 206 to enhance rhodium stability.

As shown in FIG. 2, carbonylation product (i.e., reaction solution) is drawn off the eductor-based reactor 205 via line 211 at a rate sufficient to maintain a constant level in reactor 205. The reaction solution of line 211 is preferably a liquid stream withdrawn from reactor 205 below the liquid level 1. In some embodiments, as the reaction solution is withdrawn via line 211 from the eductor-based reactor 205, the temperature of the reaction solution may be from about 150° C. to about 250° C. Some or all of the reaction solution may be transported to flasher 206 via line 211, past T-connection 212 and via line 213. In flasher 206, the carbonylation product is separated in a flash separation step to obtain a crude product stream 214 comprising acetic acid and a catalyst recycle stream 215 comprising a catalyst-containing solution. Crude product stream 214 is transferred to the purification section (not shown) of the carbonylation system for recovering acetic acid. In some embodiments, one or more recycle streams from the purification section may be returned to the eductor-based reactor 205 via line 208. In preferred embodiments, catalyst recycle stream 215 is recycled to eductor-based reactor 205. The catalyst-recycle stream 215 predominantly contains acetic acid, the catalyst and the halogen promoter, along with lesser quantities of methyl acetate, methyl iodide and water.

The flow rate of the reaction solution that is withdrawn from the eductor-based reactor 205 via line 211 is a function of production rate, among other variables, and may vary. In some embodiments, a portion of the reaction solution may be withdrawn at T-connection 212 via line 221 and pass through one or more pump around loops 220. The amount of the reaction solution withdrawn as pump around stream via line 221 may be from 20% to 100%, e.g., from 30% to 80% or from 40% to 60%, of the total amount of the reaction solution based on the controlled level of reactor 205 and temperature and production rate of operation or non-steady state operation (e.g., during reactor start up). Preferably, under steady state operation conditions, at least 50%, e.g., at least 54% or at least 60% of the reaction solution is withdrawn as pump around streams. The portion of reaction solution withdrawn at T-connection 212 as pump around stream 221 may be an aliquot portion of the reaction solution and may comprise one or more of catalyst, dissolved/entrained carbon monoxide and reaction gases, one or more reactants, water, acetic acid, and/or halogen promoters. Although line 221 is shown in FIG. 2, it should be understood that there may be several lines and several pump around loops encompassed by the present invention. For example, in an optional embodiment not shown in FIG. 2, a pump around loop may be sourced from a nozzle located on reactor 205 below liquid level 1.

Pump around loop 220 comprises at least one pumping system 222. In preferred embodiments, pumping system 222 comprises a plurality of pumps. Preferably, there also may be several pumping systems, valves and controls arranged in series or in parallel for controlling the flow of the pump around loop 220. Pump around stream 221 withdrawn from the reaction solution at T-connection 212 may have a substantially similar flow rate or a lower flow rate than the reaction solution in line 211. In some embodiments, the flow rate of the pump around streams may be greater than the flow rate of the reaction solution in line 213 forwarded to flasher 206. In certain embodiments, the flow rate of pump around stream 221 is at least 1.2 times greater than the flow rate of the reaction solution in line 213, e.g., at least 1.5 times greater, at least 2 times greater, at least 3 times greater or at least 4 times greater. For example, when the flow rate of the reaction solution in line 213 is 100 tns/hr, then the pump around streams may have a total flow rate of at least 120 tns/hr, e.g., at least 150 tns/hr or 200 tns/hr. In a preferred embodiment, the pump around streams may have a flow rate of at least 800 tns/hr. In addition, under normal steady-state operation of the eductor-based reactor in production mode, the flow rates through each pump around loop A, B, and/or C streams 223, 232, and 242 may also vary. In some embodiments, the flow rate may be divided in substantial equal portions to each of loops A, B, and/or C.

After being fed to pumping system 222, pump around streams may be returned to reactor 205 by loop A, loop B and/or loop C, as shown in FIG. 2. In one embodiment, all of the pump around stream may be returned through one of loop A, loop B or loop C and preferably, pump around streams are recycled from/to reactor 205 in the process. In other embodiments, a portion of pump around stream may be returned through loop B and another portion through loop A and/or loop C. In still other embodiments, a portion of pump around stream may be returned through loop A and another portion through loop C. One or more pumping systems 222 (e.g., plurality of variable speed pumps) and valves may be used to regulate the flow of pump around stream to loops A, B and/or C.

Eductor-based reactor 205 may be similar to the reactor described above and shown in FIGS. 1A and 1B. For purposes of clarity, in FIG. 2, eductor-based reactor 205 comprises at least a supply pipe 217, manifold 218 and one or more eductor mixers 219. Each of the pump around streams may be returned to eductor-based reactor 205 through supply pipe 217 and to eductor mixers 219. As pump around stream 221 passes through pumping system 222 into loops A, B and/or C, the pressure of the pump around stream is boosted. In one embodiment, the positive change in pressure of the pump around stream prior to entering eductor-based reactor 205 may be from 0.7 barg to 7.0 barg, e.g., 1.5 barg to 5.5 barg or 2.5 barg to 4.0 barg, compared to the reaction medium (i.e., secondary fluid) within reactor 205. The boosted-pressure, pump around stream may be discharged from each of the eductor mixers 219 into the reaction medium to create continuous turbulence and provide targeted and thorough mixing of the reaction medium.

Loop A comprises line 223 that directly feeds pump around stream to supply pipe 217. In loop A, there are no heat exchangers and/or steam generators.

Loop B comprises one or more steam generators 230 and/or one or more heat exchangers 231. For purposes of clarity, one steam generator 230 and heat exchanger 231 is shown in FIG. 2. Additional steam generators and/or heat exchanges may be used in other embodiments of the present invention. Depending on the flow rate, a portion of the pump around stream in line 232 may be directed to steam generator 230 or heat exchanger 231. In one embodiment, all of pump around stream in line 232 may be directed to steam generator 230 via line 233. In preferred embodiments, greater flow rates of the pump around stream in line 232 may be able to generate greater quantity and quality steam in steam generator 230. Steam generator 230 has an exiting process stream 234 that may be returned to reactor 205 via supply pipe 217. Optionally, a portion of exiting process stream 234, e.g., from 5%-95%, may be directed via line 235 to heat exchanger 231. Loop B may also direct all of pump around stream in line 232 to heat exchanger 231 and bypass steam generator 230 via line 236. The outflow of heat exchanger 231 may be directed to supply pipe 217 of reactor 205 via line 237.

Loop C comprises one or more steam generators 240 and one or more heat exchangers 241. For purposes of clarity, one steam generator 240 and heat exchanger 241 is shown in FIG. 2. However, additional steam generators and/or heat exchanges may be used in embodiments of the present invention. In some embodiments, the exiting process stream 243 of steam generator 240 may pass through heat exchanger 241, and the outflow of heat exchanger 241 is returned to supply pipe 217 of reactor 205 via line 244. In certain embodiments, a portion of stream 244, e.g., from 5%-95%, is directed into stream 245 via line 246 in order to control the amount of feed sent to reactor 205. In other embodiments, a portion of exiting process stream 243, e.g., from 5%-95%, may be directly returned to reactor 205 via line 245, without passing through eductor mixers 219 and/or heat exchanger 241.

In some embodiments, when pump around stream is directed to loops B and/or C, it is preferred to have a flow rate of the pump around stream that is at least four times greater than the flow rate of the reaction solution in line 213, e.g., at least five times greater or at least eight times greater.

Steam generators used in embodiments of the present invention preferably are capable of generating high quantities and variable qualities (i.e., pressure) of steam. Certain embodiments of the present invention enable the generation of high quantity, variable quality steam to supply up to 100%, e.g., up to 80% or up to 50%, of steady state steam demand for the processes of the purification section of the carbonylation system. In addition, the steam may be used to supply other systems in the carbonylation process, e.g., turbine driven pumps, to flare (to induce mixing), to heat storage tanks, or other chemical units, such as, for example, anhydride production units and/or ester units. In preferred embodiments, each pump around loop produces at least 5 tns/hr of steam, e.g., at least 15 tns/hr or at least 25 tns/hr. In terms of ranges, each pump around loop may produce from 5 tns/hr to 30 tns/hr, e.g., from 5 tns/hr to 25 tns/hr or 20 tns/hr to 25 tns/hr. In terms of flow rate with reference to flow rate forward to flasher 206 in line 213, the quantity of steam generated by each pump around loop may be from 0.01x to 1x tns/hr, e.g., from 0.02x to 0.5x tns/hr or from 0.03 to 0.1x tns/hr. In addition, in preferred embodiments, the steam produced has a pressure of at least 3.5 barg, e.g., at least 5 barg, or at least 6 barg. The quantity of steam produced by the steam generators from the pump around stream may vary based on the flow rate, temperature in the carbonylation system, and the pressure quality of the steam being generated. Greater flow rates in one or more of the pump around streams may produce higher quantity and/or quality steam. Because it may be advantageous in some embodiments to have greater flow rates of the pump around stream to effectuate mixing by the eductor mixers, it is also preferred to recover the heat from the pump around stream to generate steam.

During normal steady-state operation of the eductor-based reactor in production mode, the pump around stream when withdrawn from the reaction solution may have a temperature from about 160° C. to about 250° C., e.g., from 175° C. to 235° C., or from 180° C. to 220° C. After passing through one of the steam generators, the exiting process stream may have a temperature below the carbonylation reaction temperature, e.g., below about 185° C., or from 150° C. to 185° C. These ranges may vary during start up or under unsteady-state reactor conditions.

Suitable steam generators may include a shell and tube exchanger, double pipe exchanger, spiral plate exchanger, plate heat exchanger, helical coil, spiral coil or bayonet tube in tank heat exchanger, or any other suitable heat exchanger known in the art. The process surface of the steam generator can be comprised of any suitable material known in the art, for example a nickel-molybdenum alloy such as HASTELLOY™ B-3™ alloy (Haynes International) or a zirconium alloy such as Zirc™ 702 alloy (United Titanium Inc.). The steam (i.e., water) side of the steam generator can be comprised of any suitable metal, including carbon steel and lower grade stainless and alloy steels, among others.

Optionally, a pump around reactor may be integrated with one or more of the steam generators to recover available heat for the production of steam. A pump around reactor may increase the temperature of the pump around stream by a secondary carbonylation reaction. An increase in temperature may result in increase steam generation. The pump around stream contains unreacted methanol and dissolved carbon monoxide, as well as catalyst, that may be further reacted. Additional reactants and/or carbon monoxide may be fed to the pump around reactor. For example, in some embodiments, a pump around reactor may be added prior to steam generators 230 (loop B) and/or 240 (loop C). A suitable pump around reactor may be a pipe reactor, tubular reactor, fluidized bed, CSTR, bubble-column type vessel or a secondary eductor-based reactor. In accordance with some embodiments of the present invention, the pump around reactor may contain mixing modifiers such as, for example, baffles or other anti-vortex devices, packing, distributors, and/or multiple passes.

Heat exchangers in loops B and/or C may include a shell and tube exchanger, spiral plate heat exchanger, helical coil exchanger, or any other suitable heat exchanger known in the art. Sensible cooling water heat exchangers are preferred. These heat exchangers preferably provide trim cooling to remove the heat of the reaction from the carbonylation reaction of the system, e.g., from eductor-based reactor 205, and provide enhanced reactor temperature control. In addition, in some embodiments, the heat exchangers may also produce steam, such as by superheating cooling water at an elevated pressure and then discharging into a lower pressure steam/condensate vessel. After passing through one of the heat exchangers, the outflow may have a temperature below the carbonylation reaction temperature, e.g., below about 155° C., or from 30° C. to 155° C.

During start up, it is initially preferred that about 100% of the reaction solution withdrawn via line 211 is directed to pump around loop 221. One or more of the pump around loops, preferably loop B or loop C, may be used to heat the reaction solution. During start up eductor-based reactor 205, the reaction medium is heated using a start up heater to about 150° C., or in other embodiments higher than 150° C. In the embodiment of the invention shown in FIG. 2, the function of the start up heater would be accomplished by steam generator 230 (loop B) or 240 (loop C), with downstream heat exchangers 231 and 241 process flow bypassed. In other embodiments, it is possible to pipe heat exchanger 231 to function as a start up steam heater. In some start up embodiments, a small quantity of carbon monoxide may be injected at one or more locations in the pump around loop. Under design rate, steady state conditions, it is preferred that less than 50% of reaction solution 211 be directed to the one or more pump around loops via line 221. In certain embodiments, less than 30%, e.g., less than 25%, of reaction solution 211 is withdrawn at T-connection 212 as the pump around stream.

Although it is shown in FIG. 2 that one portion of the reaction solution 211 is withdrawn, multiple portions may be taken and separately provided to one or more pump around loops. In addition to loops A, B, C, there may be any number of loops included in the carbonylation system. In preferred embodiments of the present invention, there is at least one loop that comprises a heat exchanger and/or steam generator.

In accordance with various embodiments of the invention, although not depicted in FIG. 2, one or more valves, regulators or pumps may be used to control fluid flow in the carbonylation system. Similarly, in other embodiments of the invention, a combination of manual and automatic isolation valves can be included in the pump around loops to allow for independent isolation of one loop (e.g., for maintenance), while the other loop(s) and eductor-based reactor 205 remain operational. In addition, in various embodiments of the invention, one or more additional heat exchangers may be present in locations throughout the system.

EXAMPLES

The present invention will be better understood with reference to the specific embodiments set forth in the following non-limiting examples.

Example 1

Figure 3:
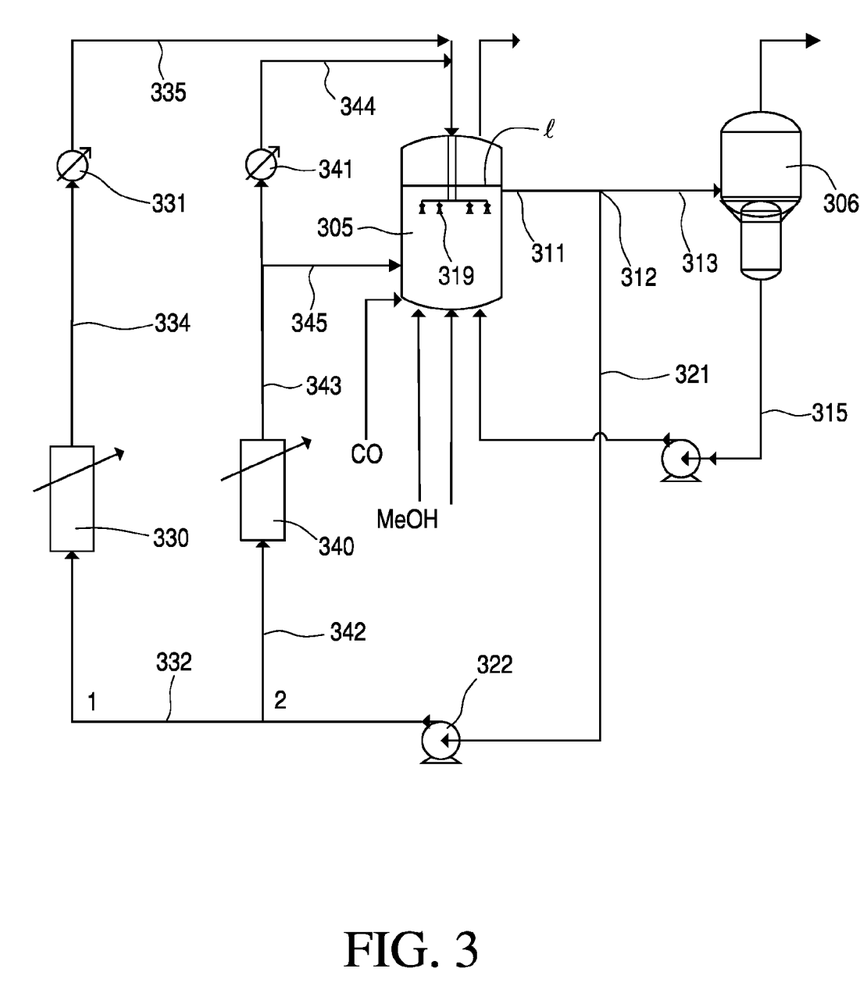
FIG. 3 is an exemplary schematic diagram illustrating various production and steam generation capabilities of an acetic acid production system having an eductor-based reactor and pump around loops in accordance with one embodiment of the present invention.

This example illustrates an acetic acid production system operating at maximum production and maximum steam generation rates. As shown in FIG. 3, reaction solution is drawn off eductor-based reactor 305 via line 311 at a rate of 6x tns/hr. Reaction solution has a temperature of 210° C.-215° C. when withdrawn from reactor 305. At T-connection 312, reaction solution is separated into a pump around stream 321 having a flow rate of 4x tns/hr and a forward feed in line 313 having a flow rate of 2x tns/hr fed to flasher 306. To maintain a mass balance of the system, recycled streams from flasher 206 in line 315 and the purification system, along with fresh CO and reactants, should be substantially similar to the forward feed of 2x tns/hr.

After stream 321 is fed to pumping system 322, the pump around streams are returned to reactor 305 by loop 1 and loop 2, as shown in FIG. 3. Stream 321 may be divided in substantial equal portions and 2x tns/hr may be directed to each loop. In loop 1, the pump around stream in line 332 is first directed to steam generator 330 to produce steam at a rate of 0.03x tns/hr to 0.04x tns/hr at 8.5 barg. Steam generator 330 has an exiting process stream that may be directed via line 334 to a cooling water heat exchanger 331. The outflow of heat exchanger 331 in line 335 has a temperature of 125° C.-145° C. The positive delta in pressure of the outflow in line 335 may be 2.5 barg-4 barg greater the pressure of eductor-based reactor 305. The outflow in line 335 is fed directly to the eductor mixers 319 in reactor 305. In loop 2, the pump around stream in line 342 is directed to steam generator 340 at a rate of 2x tns/hr. Steam generator 340 produces steam at a rate of about 0.03x tns/hr to 0.04x tns/hr at 8.5 barg. 20-50% of exiting process stream 343 of steam generator 340 passes through heat exchanger 341. The outflow of heat exchanger 341 in line 344 has a temperature of 60° C.-80° C. The positive delta in pressure of the outflow in line 344 may be 2.5 barg-4 barg greater the pressure of the reactor 305. The outflow in line 344 is fed directly to the eductor mixers 319 in reactor 305. The remaining 50-80% of exiting process stream 343 passes directly into reactor 305 below liquid level l.

Example 2

This example demonstrates that while operating at half the production rate of Example 1, large quantities of high quality steam can nevertheless be produced. As depicted in FIG. 3, reaction solution is drawn off eductor-based reactor 305 in line 311 at a rate of 5x tns/hr. Pump around stream 321 is withdrawn from the reaction solution in line 311 at T-connection 312 at a flow rate of 4x tns/hr. The remaining portion of the reaction solution in line 311 is transported to flasher 306 via line 313 at a rate of x tns/hr. The recycle streams in line 315 and from the purification system along with fresh CO and reactants have a flow rate of x tns/hr.

Stream 321 is fed to loop 1 and loop 2 in a manner similar to that described in Example 1. Loop 1 generates a similar quantity and quality of steam as in Example 1, from 0.03x tns/hr to 0.04x tns/hr at 8.5 barg. Temperature of the outflow in line 335 is 125° C.-145° C. Loop 2 also generates a similar quantity and quality of steam as in Example 1, from 0.03x tns/hr to 0.04x tns/hr at 8.5 barg. In this embodiment, about 100% of outflow 343 is directed to line 345. Minimal to no flow is directed through exchanger 341.

Example 3

This example demonstrates operation of an acetic acid production system at maximum production rates and relatively low steam production rates. As depicted in FIG. 2, reaction solution is drawn off eductor-based reactor 205 via line 211 at a rate of 4x tns/hr. Pump around stream 221 is withdrawn from the reaction solution in line 211 at T-connection 212 and possesses a flow rate of 2x tns/hr. The remaining portion of the reaction solution in line 211 is transported to flasher 206 via line 213 at a rate of 2x tns/hr. To maintain mass balance, recycled streams from flasher in line 215 and the purification system in line 208, along with fresh CO and reactants, should be substantially similar to the forward feed of 2x tns/hr.

After stream 221 is fed to pumping system 222, the pump around streams are returned to reactor 205 by loop B and by loop C. In loop B, the pump around stream in line 232 is bypass directed around steam generator 230 via line 236 at a rate of x tns/hr. Process stream is directed via line 236 to cooling water heat exchanger 231. The outflow of heat exchanger 231 in line 237 has a temperature of 65-95° C. The positive delta pressure of the outflow in line 237 may be 2.5 barg-4 barg greater than the pressure of reactor 205. The outflow in line 237 is fed directly to the eductor mixers 219 in reactor 205. In loop C, the pump around stream in line 242 is directed to steam generator 240 at a rate of x tns/hr. Steam generator 240 produces steam at a rate of about 0.02x tns/hr to 0.04x tns/hr at 8.5 barg. 100% of exiting process stream 243 of steam generator 240 passes through heat exchanger 241. The outflow of heat exchanger 241 in line 244 has a temperature of 65° C.-95° C. The positive delta pressure of the outflow in line 244 may be 2.5 barg-4 barg greater the pressure of reactor 205. Outflow in line 244 is fed directly to the eductor mixers 219 in reactor 205.

Example 4

Figure 4:
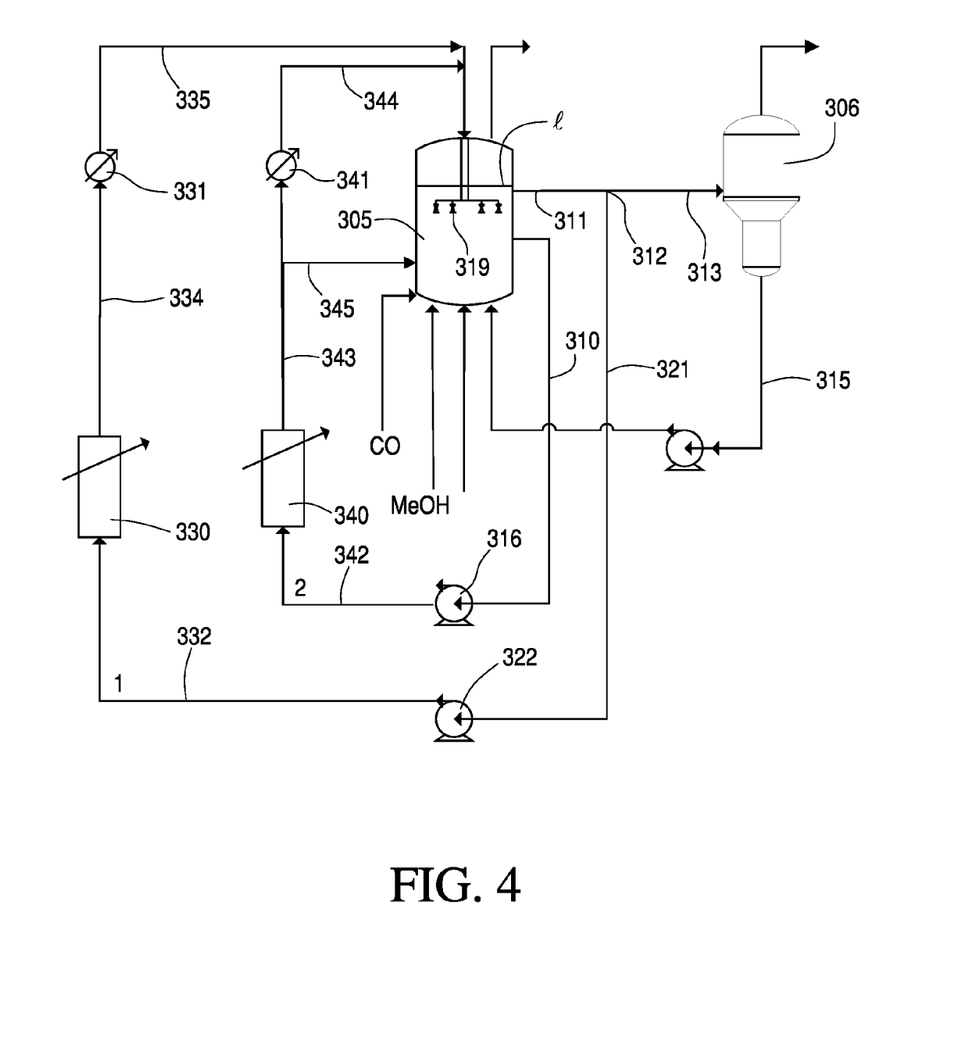
FIG. 4 is an exemplary schematic diagram for acetic acid production having an eductor-based reactor and pump around loops, with a pump around loop sourced directly from the reactor, in accordance with one embodiment of the present invention.

This example demonstrates an embodiment of the present invention where a pump around loop is sourced from a nozzle located on the eductor-based reactor. As shown in FIG. 4, reaction solution is drawn off eductor-based reactor 305 via line 311 at a rate of 3x tns/hr. In addition, reaction solution is drawn off eductor-based reactor 305 via a nozzle positioned below liquid level l leading to line 310 at a rate of 2x tns/hr. Pump around stream 321 is withdrawn from the reaction solution in line 311 at T-connection 312 at a rate of 2x tns/hr. The total flow through combined pump around streams via line 310 and line 321 may be 4x tns/hr. At T-connection 312, the remaining portion of the reaction solution in line 311 is transported to flasher 306 via line 313 at a rate of x tns/hr and catalyst recycle stream 315 from flasher 306, along with other recycle streams 316 and fresh CO and reactants, is recycled to eductor-based reactor 305 at a rate of x tns/hr.

After stream 321 is fed to pumping system 322, the pump around stream is returned to reactor 305 by loop 1 at a flow rate of 2x tns/hr. In loop 1, the pump around stream in line 332 is directed to steam generator 330 to produce steam at a rate of 0.02x tns/hr to 0.04x tns/hr at 8.5 barg. Steam generator 330 has an exiting process stream that is directed via line 334 to cooling water heat exchanger 331. The outflow of heat exchanger 331 in line 335 has a temperature of 125° C.-145° C. The positive delta pressure of the outflow in line 335 may be 2.5 barg-4 barg greater than the pressure of eductor-based reactor 305. Outflow in line 335 is fed directly to the eductor mixers 319 in reactor 305.

Stream 310 is fed to pump 316, and the pump around stream is returned to reactor 305 by loop 2 at a flow rate of 2x tns/hr. In loop 2, the pump around stream in line 342 is directed to steam generator 340. Steam generator 340 produces steam at a rate of about 0.03x tns/hr to 0.04x tns/hr at 8.5 barg. 20-50% of exiting process stream 343 of steam generator 340 passes through cooling water heat exchanger 341. The outflow of heat exchanger 341 in line 344 has a temperature of 65° C.-95° C. The positive delta pressure of the outflow in line 344 may be 2.5-4 barg greater than the pressure of reactor 305. The outflow in line 344 is fed directly to the eductor mixers 319 in reactor 305. The remaining 50-80% of exiting process stream 343 passes directly into reactor 305 via line 345 below liquid level l.

In the interest of clarity, not all features of an actual implementation for the processes used to carbonylate methanol to acetic acid are described in this specification. Parameters such as the residence time in the pump around loop and measured temperatures, flow(s) and/or measured pressures with controlled raw material flow rate additions may be optimized to a desired configuration. It will be appreciated by those of skill in the art that in the development of any such actual embodiment, numerous implementation-specific decisions must be made to achieve the specific goals, such as compliance with system-related and business-related constraints, which will vary from one implementation to another. Moreover, it will be appreciated that such a development effort may be complex and time-consuming, but would nevertheless be a routine undertaking for those of ordinary skill in the art having the benefit of this disclosure.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. Furthermore, those of ordinary skill in the art will appreciate that the foregoing description is by way of example only, and is not intended to limit the invention.

The invention claimed is:

1. A process for producing acetic acid, comprising the steps of:
   reacting carbon monoxide with at least one reactant in a eductor-based reactor containing a liquid reaction medium to produce a reaction solution comprising acetic acid, wherein the at least one reactant is selected from the group consisting of methanol, methyl acetate, methyl formate, dimethyl ether and mixtures thereof, and wherein the liquid reaction medium comprises water, acetic acid, methyl acetate, methyl iodide, and a catalyst, wherein the eductor-based reactor comprises one or more eductor mixers;
   separating a portion of the reaction solution to form a pump around stream; and
   feeding a portion of the pump around stream to at least one of the one or more eductor mixers to provide mixing of the reaction medium in the eductor-based reactor.

2. The process of claim 1, further comprising the step of:
   feeding the remaining portion of the reaction solution withdrawn from the reactor but not separated to form the pump around stream forward to a flasher to produce a crude product and a catalyst recycle stream, wherein the pump around stream is separated prior to the introduction to the flasher.

3. The process of claim 2, wherein the flow rate of the pump around stream is at least 1.2 times greater than the flow rate of the remaining portion of the reaction solution forwarded to the flasher.

4. The process of claim 1, further comprising the step of:
   passing a portion of the pump around stream through one or more steam generators to produce an exiting process stream and steam.

5. The process of claim 4, further comprising the step of:
   feeding a portion of the exiting process stream to at least one of the one or more eductor mixers to provide mixing of the reaction medium in the eductor-based reactor.

6. The process of claim 4, wherein the exiting process stream has a temperature that is less than the temperature of the reaction solution withdrawn from the eductor-based reactor.

7. The process of claim 1, further comprising the step of:
   passing a portion of the pump around stream through one or more heat exchangers to produce an outflow.

8. The process of claim 7, further comprising the step of:
   feeding a portion of the outflow to at least one of the one or more eductor mixers to provide mixing of the reaction medium in the eductor-based reactor.

9. The process of claim 1, wherein 20% to 100% of the reaction solution withdrawn from the eductor-based reactor is separated as the pump around stream.

10. The process of claim 1, wherein at least 50% of the reaction solution withdrawn from the eductor-based reactor is separated as the pump around stream.

11. The process of claim 1, wherein the one or more eductor mixers each have a discharge to motive flow rate ratio of at least 2:1.

12. A process for producing acetic acid, comprising the steps of:
    reacting carbon monoxide with at least one reactant in a reactor containing a liquid reaction medium to produce a reaction solution comprising acetic acid, wherein the at least one reactant is selected from the group consisting of methanol, methyl acetate, methyl formate, dimethyl ether and mixtures thereof, and wherein the liquid reaction medium comprises water, acetic acid, methyl acetate, methyl iodide, and a catalyst;
    withdrawing the reaction solution at a first flow rate from the reactor;
    separating a portion of the reaction solution to form a pump around stream;
    separating a remaining portion of the reaction solution withdrawn from the reactor but not separated to form the pump around stream and forwarding the remaining portion to a flasher, wherein the flow rate of the pump around stream is at least 1.2 times greater than the flow rate of the remaining portion of the reaction solution forwarded to the flasher;
    passing a portion of the pump around stream through one or more steam generators to produce an exiting process stream and steam; and
    feeding a portion of the exiting process stream to the reactor.

13. The process of claim 12, wherein the reactor is an eductor-based reactor, and wherein the eductor-based reactor comprises one or more eductor mixers.

14. The process of claim 13, further comprising the step of:
    feeding a portion of the exiting process stream to at least one of the one or more eductor mixers to provide mixing of the reaction medium in the eductor-based reactor.

15. The process of claim 12, further comprising the step of:
    passing a portion of the exiting process stream through one or more heat exchangers to produce an outflow.

16. The process of claim 12, further comprising the step of:
    introducing the remaining portion of the reaction solution to the flasher to produce a crude product and a catalyst recycle stream, wherein the pump around stream is separated prior to the introduction to the flasher.

17. A process for producing acetic acid, comprising the steps of:
    reacting carbon monoxide with at least one reactant in a reactor containing a liquid reaction medium to produce a reaction solution comprising acetic acid, wherein the at least one reactant is selected from the group consisting of methanol, methyl acetate, methyl formate, dimethyl ether and mixtures thereof, and wherein the liquid reaction medium comprises water, acetic acid, methyl acetate, methyl iodide, and a catalyst;
    withdrawing the reaction solution at a first flow rate from the reactor;
    separating a portion of the reaction solution to form a pump around stream;
    separating a remaining portion of the reaction solution withdrawn from the reactor but not separated to form the pump around stream and forwarding the remaining portion to a flasher, wherein the flow rate of the pump around stream is at least 1.2 times greater than the flow rate of the remaining portion of the reaction solution forwarded to the flasher;
    passing a portion of the pump around stream through one or more heat exchangers to produce an outflow; and
    feeding a portion of the outflow to the reactor.

18. The process of claim 17, wherein the reactor is an eductor-based reactor, and wherein the eductor-based reactor comprises one or more eductor mixers.

19. The process of claim 18, further comprising the step of:
    feeding a portion of the outflow to at least one of the one or more eductor mixers to provide mixing of the reaction medium in the eductor-based reactor.

20. The process of claim 17, further comprising the step of:
    passing a portion of the pump around stream through one or more steam generators to produce an exiting process stream and steam.

21. The process of claim 17, further comprising the step of:
introducing the remaining portion of the reaction solution to the flasher to produce a crude product and a catalyst recycle stream, wherein the pump around stream is separated prior to the introduction to the flasher.

22. The process of claim 1, wherein the catalyst is a homogeneous catalyst.

* * * * *